US011976325B2

(12) United States Patent
Meltzer (10) Patent No.: US 11,976,325 B2
(45) Date of Patent: May 7, 2024

(54) QUANTITATIVE DETECTION AND ANALYSIS OF MOLECULES

(71) Applicant: FLUENT BIOSCIENCES INC., Watertown, MA (US)

(72) Inventor: Robert Meltzer, Belmont, MA (US)

(73) Assignee: FLUENT BIOSCIENCES INC., Watertown, MA (US)

( * ) Notice: Subject to any disclaimer, the term of this patent is extended or adjusted under 35 U.S.C. 154(b) by 0 days.

(21) Appl. No.: 18/131,624

(22) Filed: Apr. 6, 2023

(65) Prior Publication Data

US 2024/0117423 A1 Apr. 11, 2024

Related U.S. Application Data

(60) Provisional application No. 63/413,786, filed on Oct. 6, 2022.

(51) Int. Cl.
*C12Q 1/6874* (2018.01)
(52) U.S. Cl.
CPC .................................. *C12Q 1/6874* (2013.01)
(58) Field of Classification Search
CPC .. C12N 2310/00; C12N 2310/14; C12Q 1/68; C12Q 2561/00; C12Q 2563/14
USPC ...................................................... 250/559.4
See application file for complete search history.

(56) References Cited

U.S. PATENT DOCUMENTS

| | | | |
|---|---|---|---|
| 10,144,957 B2 * | 12/2018 | Rabbani | C12Q 1/6818 |
| 10,731,213 B2 * | 8/2020 | Cantor | C12Q 1/6876 |
| 11,467,153 B2 * | 10/2022 | Belhocine | C12Q 1/6806 |
| 2016/0053253 A1 | 2/2016 | Salathia et al. | |
| 2018/0320224 A1 | 11/2018 | Gaublomme et al. | |
| 2021/0340596 A1 | 11/2021 | Meltzer et al. | |
| 2022/0135966 A1 | 5/2022 | Meltzer | |

FOREIGN PATENT DOCUMENTS

WO 2022031955 A1 2/2022

* cited by examiner

*Primary Examiner* — Seung C Sohn
(74) *Attorney, Agent, or Firm* — Withers Bergman, LLP; Thomas C. Meyers (57) ABSTRACT

The invention provides systems and methods for making sequencing libraries that are useful for quantitatively analyzing nucleic acids in a sample. Sample nucleic acids are randomly cleaved at, and PCR handled are attached to, a random cut site. The nucleic acid is amplified into a sequencing library in which a sequencing primer generates a sequence read from adjacent the random cut site. The sequence reads can be mapped to a reference, but they will also include a unique identifier sequence that comes from within the nucleic acid molecule being analyzed, i.e., an intrinsic molecular identifier (IMI). The IMI is unique for each molecule and can thus be used to deduplicate sequence reads originating from the same molecule.

23 Claims, 5 Drawing Sheets

QUANTITATIVE DETECTION AND ANALYSIS OF MOLECULES

TECHNICAL FIELD

The invention relates to the quantitative detection and analysis of molecules in a sample such as a single cell.

BACKGROUND

Living organisms store genetic information in DNA. Genes in the coding regions of DNA are transcribed into messenger RNA (mRNA), which is translated into protein. Proteins play critical functional and structural roles in living organisms. For example, most enzymes are proteins, and those enzymes catalyze the metabolic reactions essential to life. It is also enzymes that copy DNA into mRNA. Proteins are also structural, and constitute the essential fibers of muscles, the predominant material of hair, as well as basic structural linkages within the cytoskeleton. Essentially, all such proteins are made by translating an mRNA into the protein. In fact, one mRNA can serve as the template for synthesizing multiple copies of a protein.

Because cells need to change in response to different conditions, and need different proteins at different times, it is helpful if any given mRNA is short-lived. Most mRNA molecules have a lifetime measured in seconds or minutes. Nevertheless, the health of a cell, or its response to a pathogen, or a drug, or to age-specific developmental changes may be indicated by the quantities of mRNA molecules present in a cell. As a consequence, there is a need for methods to sequence, quantitate, and evaluate cellular RNA. That is usually accomplished by creating so-called sequencing libraries, arrays of complementary DNA (cDNA) reverse transcribed from cellular RNA. The cDNA is sequenced via one of several procedures and the whole process can take days or even weeks to complete. There is, therefore, a continuing need for improved methods for identifying and evaluating cellular RNA in a rapid, sensitive, and specific fashion.

SUMMARY

The invention provides systems and methods for making sequencing libraries that are useful for analyzing and determining quantities of nucleic acids in a sample including for measuring mRNA transcript levels in a single cell. Methods and systems of the invention provide each nucleic acid in a sample with a unique label during preparation of a sequencing library. When the nucleic acids are sequenced, sequence data includes the unique label, allowing sequence reads to be deduplicated by those labels, leaving one unduplicated sequence for each molecule in the original sample. The unduplicated sequences represent a quantitative measure of nucleic acids in the starting sample. Where, for example, the sample includes messenger RNA transcripts from a cell, the sequence reads can be mapped to a reference to identify genes being expressed in a cell. But the sequence reads can also be deduplicated by the unique label to give a measure of transcripts from each gene, i.e., giving gene expression levels for the cell.

According to the invention, the unique label is provided as sequence that is intrinsic to the nucleic acid being analyzed. Compared to prior methods that required the attachment of large numbers of synthetic unique molecular identifiers (UMIs) to all of the nucleic acid molecules, the present invention uses random cleavage or priming of sample nucleic acids, at a random cutting or priming site, leaving those nucleic acids with essentially unique segments adjacent that random cut site. Adaptors or PCR handles are attached at the random sites and library preparation steps, such as amplification or sequencing proceed by annealing primers to those PCR handles. Amplification provides sequencing libraries in which a sequencing primer anneals in the adaptor or PCR handle and generates a sequence read from adjacent the random site. With paired-end sequencing, only one sequence read need begin at the random site. The sequence reads can be mapped to a reference, and they will include a unique identifier sequence that comes from within the nucleic acid molecule being analyzed, i.e., an intrinsic molecular identifier (IMI). The IMI is unique for each molecule and can thus be used to deduplicate sequence reads originating from the same molecule.

In certain aspects, the invention provides systems for nucleic acid analysis. Systems of the invention include a solid support having attached thereto a plurality of DNA molecules, each member of the plurality comprising a capture sequence, a segment of DNA containing an identifier sequence that is intrinsic to the segment of DNA and unique with respect to other DNA molecules attached to the same or a different solid support, and a primer binding sequence.

The intrinsic identifier sequence may be from about 5 to about 20 base pairs in length. The DNA may come from a coding region. Systems may include a linker for attachment (e.g., covalent) to the solid support. In systems of the invention, the primer binding sequence may be ligated to the DNA using transposase such as Tn5. In certain embodiments, the capture sequence hybridizes with a portion of an RNA, e.g., such as a poly-T region when the DNA is a cDNA. The transposase cleaves the DNA (e.g., at a random site) to generate the identifier sequence and may insert a paired-end sequence or similar primer binding site or sequencing adaptor (e.g., at the random site.

Aspects of the invention provide a system for nucleic acid analysis that includes a solid support and a nucleic acid construct attached to the solid support, such as a bead. The nucleic acid construct includes a linker for attachment to the solid support, a cell-identification barcode, a capture region, and a region of cDNA comprising a portion in which a unique identifier sequence that is intrinsic to the cDNA has been generated. Preferably, the region of cDNA has been randomly cleaved at a cut site, and a synthetic oligo has been attached at the cut site. The system may include a transposase that functions to cleave the cDNA or a primer that primes at an essentially random location, thereby generating the unique identifier sequence, and a paired-end sequence (or similar synthetic oligo) for hybridization to a sequencing surface. Preferably the transpose cleaves the cDNA at a cut site that is random or cannot be predicted and attaches the paired-end sequence to the cDNA at the cut site. The unique identifier sequence is defined by a plurality of bases in a segment of the cDNA adjacent the cut site. The system may include a plurality of paired-end sequence-ligated cDNAs, e.g., all linked to the solid support and each comprising an identifier sequence in the cDNA adjacent a random cut site. In preferred embodiments, sequence reads from the plurality of cDNAs can be deduplicated to quantify RNAs captured on the solid support.

In some embodiments, the cDNA has been randomly cleaved by a restriction enzyme or sonication, and the synthetic oligo has been attached by a ligase. In embodiments, the unique identifier sequence intrinsic to the cDNA has been defined by random priming, e.g., by a random hexamer. For example, an RNA may have been captured by a random primer that was extended to create the cDNA such that the primer-binding site is random and a segment of bases in the cDNA adjacent the priming site is useful as a unique identifier sequence. In certain embodiments, the cDNA has been randomly cleaved by, and the synthetic oligo has been attached by, a ligase.

Preferably the unique identifier sequence is defined by a plurality of bases in a segment of the cDNA adjacent the cut site. The plurality of bases may be intrinsic, e.g., copied from genetic material of an organism. The system may include a plurality of the solid supports (e.g., beads), each solid support attached to cDNA copies of RNAs from a single cell, in which each cDNA copy has a unique identifier defined by bases in a segment of that cDNA copy adjacent a random cut site, such that the RNAs from a single cell can be quantified by sequencing the RNAs and deduplicating sequence reads by the unique identifier. In certain embodiments, the solid support comprises a hydrogel bead linked to a plurality of capture oligos. E.g., the system may include a plurality of the hydrogel beads, each isolated in an aqueous partition.

Other aspects of the invention provide a method for generating nucleic acid library. The method includes providing a sample comprising a plurality of cells, each comprising sample nucleic acids; hybridizing sample nucleic acids to a construct comprising a solid support to which is attached, via a linker, a cellular barcode sequence, and a capture sequence; extending said construct from said capture sequence to form a duplex comprising an extended construct; exposing said duplex to a transposase, thereby to generate a unique identifier sequence at a 3' end of said construct; and amplifying said extended construct; thereby to create a nucleic acid library. The extending step may reverse transcribe a sample nucleic acid into a cDNA in the construct. Preferably the transposase cuts the cDNA at a random cut site. The unique identifier sequence ma be provided by a segment of the cDNA adjacent the random cut site. The method may include sequencing the library to generate sequence reads, mapping the sequence reads to genes in a reference, and collapsing reads that include the same unique identifier sequence.

In some embodiments, the method includes isolating the cells into partitions and creating sequencing libraries from single cells in the partitions. The solid support may be a bead attached to a plurality of copies of the cellular barcode sequence. The method may include attaching synthetic oligos (such as paired-end sequences, PCR handles, or sequencing adaptors) at random cut sites in mRNA molecules.

In some aspects, the invention provides a method for generating a nucleic acid library. The method includes capturing RNA molecules from a single cell with capture oligos that include a first PCR handle; extending the capture oligos to form duplexes comprising the RNA molecules and cDNA; and cleaving the duplexes at, and attaching second PCR handles to, random cut sites to thereby form constructs that each include a label defined by intrinsic sequence of a cDNA segment adjacent the random cut site. The method may further include amplifying the constructs to form amplicons; sequencing the amplicons to produce sequence reads; and counting sequence reads with duplicate intrinsic sequences as one RNA molecule from the single cell. The capture oligos may be linked to a solid support in an aqueous partition that includes the single cell.

The solid support may be a bead and the aqueous partition may be a droplet. The method may include forming a plurality of droplets that each include, on average, one bead decorated with capture oligos and zero or one single cell. In some embodiments, the droplets are formed in channels of a microfluidic device. In certain embodiments the plurality of droplets are formed substantially simultaneously by shearing or vortexing a vessel comprising an aqueous phase, an immiscible phase, oligo-linked beads, and cells. The capture oligos may further include cell barcodes.

In certain embodiments, the constructs include at least the first PCR handles, the cell barcodes, cDNAs, and the second PCR handles. The amplicons may include copies of the first and second PCR handles such that the copies of the first and second PCR handles anneal to sequencing adaptors. The method may include mapping the sequence reads to a reference to identify genes from which one or more of the RNA molecules were transcribed. The method may include providing a report with transcription levels of the genes in the single cells based on the counted sequence reads and identified genes.

In some embodiments, the cleaving and/or the attaching steps are performed by an enzyme such as a transposase that creates the random cut sites. Preferably the intrinsic sequence of the cDNA is copied from genetic material of the single cell such that, due to the random cut site, each duplex includes a label useful to uniquely identify the cDNA is sequencing data.

Other aspects of the invention provide a method that includes cleaving a cDNA at, and attaching an oligo to, a random cut site; copying the cDNA to generate copies that include an intrinsic label copied from a segment of the cDNA adjacent the cut site; sequencing the copies to generate sequence reads; and collapsing duplicate sequence reads that contain the same intrinsic label. The intrinsic label may be some number of bases, e.g., between about 5 and about 30, from a segment near or adjacent the random cut site. The method may include capturing an mRNA with a capture oligo and extending the capture oligo to synthesize the cDNA. Preferably the cDNA is linked to a bead. The method may include isolating single cells into droplets, lysing the cells to release RNA into the droplets, capturing an mRNA within one of the droplets, and making the cDNA from the mRNA. The droplets may be formed simultaneously in a technique that also includes isolating the cells into the droplets (e.g., shearing a mixture that includes beads and cells in an aqueous phase plus an oil). Preferably the cleaving and the attaching at the random cut site are performed using an enzyme such as a transposase. The oligo that is attached at the random cut site may include a PCR handle used in the copying step. The attaching step may yield a DNA construct including a first priming site, a cell barcode, a portion of the cDNA, the random cut site, and a second priming site. Preferably the copying step comprises amplification by polymerase chain reaction (PCR).

DETAILED DESCRIPTION

High-throughput sequencing technologies yield vast numbers of short sequence reads from a pool of nucleic acid fragments. The invention provides sequencing applications that estimate the abundance of a particular fragment by the number of reads obtained in a sequencing experiment (read counting) using intrinsic molecular identifiers. Sequencing and read counting approaches are useful in RNA sequencing (RNA-seq), which may be used to quantify transcript abundance in a sample such as a single cell. Typical workflows involve copying RNA into cDNA, amplifying the cDNA into amplicons that include a molecular identifier copied from the RNA, and sequencing the amplicons to yield sequence reads. The molecular identifier is useful because PCR is non-uniform and neither the abundance of sequence reads nor amplicons is a measure of transcript abundance in a sample. Nucleic acid barcodes known as unique molecular identifiers (UMIs) were previously proposed as a method to count the number of mRNA molecules in a sample, e.g., by labeling PCR duplicates with a common UMI. By incorporating a UMI into each fragment during library preparation, but prior to PCR amplification, the idea was to identify PCR duplicates because they would have both identical alignment coordinates and identical UMI sequences. Unfortunately, UMIs require additional steps during sample preparation and consume "sequencing real estate". Some short-read technologies give sequence reads that can be as short as 35 bases, and some UMIs can be as long as 30 bases. Methods of the invention provide similar results without requiring the use of UMIs.

Methods of the invention are useful for creating sequencing libraries that can be sequenced to quantify molecules such as mRNA transcripts in a sample, such as the mRNAs of a single cell. Those molecules can be quantified by methods of the invention due to library preparation methods given herein that provide each molecule with a unique, intrinsic identifier, a sequence within the molecule that could be referred to as an intrinsic molecular identifier (IMI).

The molecular identifier is intrinsic in that it is made of bases that are copied from the genetic material being studied. For example, where single-cell RNA-seq (scRNA-Seq) is being performed to quantify messenger RNA (mRNA) transcripts present in a single cell, those mRNA transcripts are copied into cDNAs and a segment of, or sequence of bases from, each cDNA is used as the intrinsic molecular identifier. The sequence of bases is intrinsic in that the sequence originates as part of the genome of the organism (or virus, or other biological source material) and is produced as a cut site in the cDNA. For methods of the invention, the molecule identifier is useful to identify each cDNA because each cDNA has an intrinsic molecular identifier that is "unique", "nearly unique", or "essentially unique". One important feature is that, across all RNA molecules from a cell, those RNA molecules are copied into cDNA molecules that can be mapped to their genes of origin and in which substantially most of the cDNA molecules have a unique intrinsic molecular identifier.

That level of unique labeling is achieved by cleaving each cDNA molecule at a random site and attaching a PCR handle to the random site or by priming sample nucleic acids at random locations using, e.g., random hexamers, where the primers include a 5' tail with a PCR handle. Typically, the cDNA molecule will have a first PCR handle that has been provided as part of a capture oligo that annealed, or hybridized, to the mRNA. The capture oligo is extended by a polymerase, copying the mRNA to form the cDNA. The cDNA is then cleaved at a random cut site, and a second PCR handle is attached at the random cut site. Because the cut site or priming site is random, a segment of the cDNA adjacent to that site will include a sequence of bases that is effectively unique for that cDNA molecule.

The cDNA molecules can be amplified from the PCR handles and the amplicons can be sequenced. Sequence reads that are generated by sequencing into the cDNA from the random site will include a sequence of bases unique to that molecule, i.e., the intrinsic molecular identifier. Sequence reads can be deduplicated and/or mapped to a reference (e.g., a human genome or a gene atlas) to identify, genes. After deduplication and mapping, a count of de-duplicated (or unique) reads mapping to each gene is a measure of transcripts of that gene from that cell. Thus the de-duplicated and happed reads provide a measure of expression levels for the cell.

In preferred embodiments, methods of the invention are used to create single-cell sequencing libraries and, in particular, libraries useful in single-cell RNA-sequencing (scRNA-Seq). Some scRNA-Seq protocols involve sequencing RNA from a cell and, in most embodiments, providing a measure of gene expression levels from the sequence data. Some approaches to scRNA-Seq rely on isolating cells into droplets with the potential to assay a large number of cells per experiment. Popular droplet-based protocols include Drop-seq (described in Macosko, 2015, Highly parallel genome-wide expression profiling of individual cells using nanoliter droplets, Cell 161(5):1202-14, incorporated by reference) and inDrop (see Klein, 2015, Droplet barcoding for single-cell transcriptomics applied to embryonic stem cells, Cell 161(5):1187-201, incorporated by reference). The invention provides intrinsic molecular identifiers that may be used in such droplet-based protocols such that those protocols do not require UMIs (although, to be clear, methods of invention are perfectly compatible with the use of UMIs if one prefers).

In certain embodiments described herein, the libraries may be created with emulsions and template particles that segregate individual cells into droplets upon vortexing. The cells may be lysed inside the droplets, to release RNA. The RNA may be captured by bead-bound capture oligos that include a bead-specific, and thus a cell-specific barcode while in the droplets. The capture oligos may be extended by a reverse transcriptase, copying the RNA to yield cDNA, which is provided with PCR primer binding sites ("PCR handles"). Preferably, at least one PCR handle is attached at an essentially random location in the cDNA such that a segment of the cDNA adjacent the random location provides a identifier sequence that is unique to that molecule. Those cDNAs may be amplified and sequenced. Sequence reads from the cells may be mapped to a reference and deduplicated, providing for identification and quantification of RNA from a multitude of single cells in one experiment, in which each cell was isolated in its own aqueous partition. Accordingly, methods of the invention provide a massively parallel, analytical workflow for preparing single-cell sequencing libraries. The methods are inexpensive, scalable, and accurate, and do not require UMIs.

Figure 1:
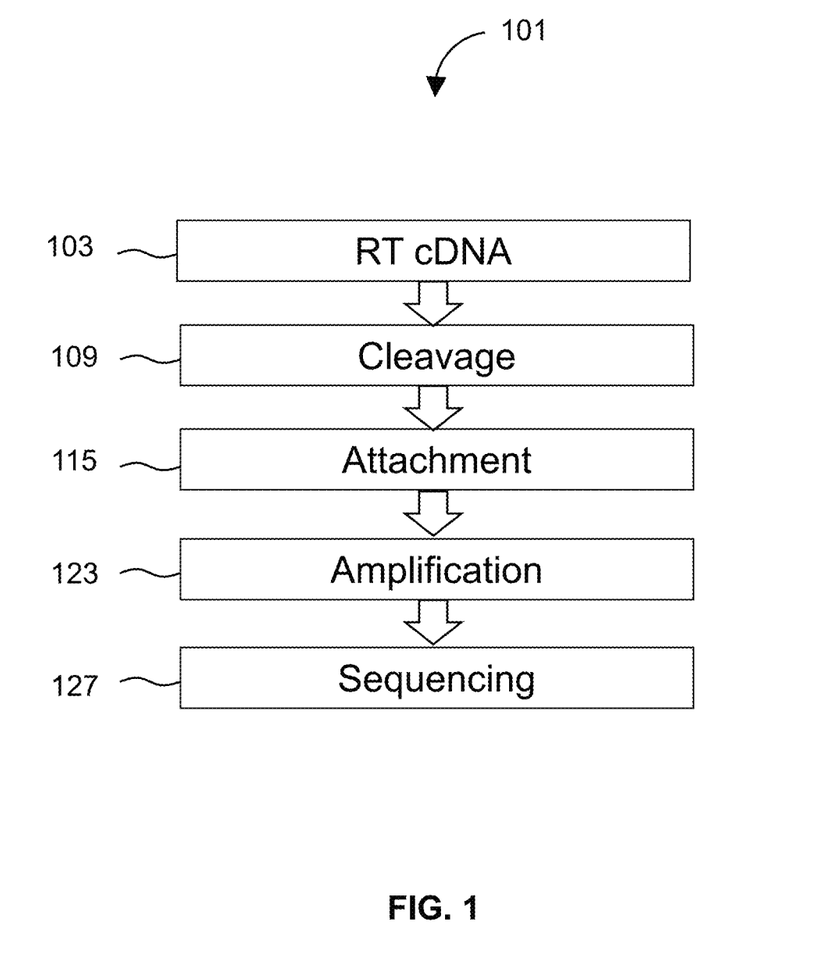
FIG. 1 diagrams a method of preparing a sequencing library.

FIG. 1 shows a block diagram of a method 101 for preparing a sequencing library. The method 101 includes reverse transcribing 103 RNA into cDNA. Each cDNAs is cleaved 109 at a random location, or "random cut site", and a synthetic oligo is attached 115 at the random cut site. Optionally or alternatively, the random site may be defined by random priming, e.g., using a random hexamer. The cleavage and attachment may be carried out by any suitable methods known in the art. For example, fragmenting 109 may be performed by physical methods, such as acoustic shearing or sonication, or by enzymatic methods, such as with a restriction enzyme, or by exposing the RNA to high temperatures, e.g., about 95 degrees Celsius, in the presence of multivalent cations, such as, metal ions, for example, Mg2+, Mn2+, or Zn2+. For example, the RNA may be incubated in a solution comprising MgCl2, at 95 degrees Celsius, for a few minutes. In preferred embodiments, the cleavage 109 and attachment 115 are performed by a transposase such as a Tn5 transposase.

Cleavage 109 according to methods of the invention generates cut sites at substantially random positions in the cDNA. Because cleavage of the cDNA is at a random cut site, the cleaved ends of the cDNA molecules are random and essentially unique. A downstream (i.e., later) step of the method involves reading sequence from the cleaved ends of the cDNA molecules. Those sequences can be treated as unique if enough bases are read from the cleaved end. That is, if there are hundreds of thousands of cDNA molecules, and only a 3-base intrinsic label is read, then there are only 64 possible unique labels. However, if 10 bases are read (assuming random use of bases) then there are greater than 1 million unique labels. Reading 12 bases gives more than 16 million labels. Fifteen bases gives more than 1 billion labels. Reading 17 bases provides more than 17 billion labels; 18 bases give >68B labels; 19 b give >274 B labels; and 20 b give >1 trillion labels. For many applications, it is not necessary that each intrinsic molecular identifier (IMI) be unique. For example, in various applications, having two, or three, or even ten IMIs that have a duplicate among the set will yield scRNA-seq quantitative results that are useful and significant, i.e., not statistically significantly different than without the duplicates for many end-uses.

A slight variant of method 101 does not use cleavage of the cDNA but instead uses primer binding at a random site such that bases that are intrinsic within the target nucleic acid adjacent the random primer binding site are copied into new DNA and come to serve as a unique intrinsic molecule identifier. These versions may use random hexamers, which are suitable as primers for capturing volumes of RNA such as mRNA from a single cell. In such embodiments, the unique identifier sequence intrinsic to the cDNA has been defined by random priming, e.g., by a random hexamer. For example, an RNA may be captured by a random primer that is extended to create a cDNA. Because random priming (e.g., using a random hexamer) binds at effectively random sites within nucleic acid, each cDNA will include a segment of bases in the cDNA adjacent the priming site that is useful as a unique identifier sequence. Random priming works similarly to random cleavage by a transpose, random mechanical or chemical cleavage, or restriction enzyme cleavage. What is in common among those techniques is that, as far as the sequences of the target nucleic acids are concerned, the binding sites or cut sites are effectively random. Each target nucleic acid will be bound or cut in manner that is unpredictable or inconsistent enough, for the purposes of techniques such as scRNA-seq, that downstream amplicons will have unique intrinsic molecular identifiers (noting again that nearly unique is sufficient for most purposes) at one end that get sequenced and appear in sequence reads.

Those intrinsic molecular identifiers of the invention may be used to establish, or contribute to, the unique molecular identity of nucleic acids of a library. For example, RNA transcribed from the same genomic loci may have sequences that are substantially identical. Here, by randomly cleaving the cDNA, each cDNA is made unique by virtue of the bases adjacent the random cut site left by the cleavage 109.

A synthetic oligo is attached 115 to the cDNA at the random cut site to create a construct that includes at least a portion of the cDNA and the synthetic oligo. Remembering that the cDNA was created by extending a capture oligo that annealed to an RNA, any sequence in the capture oligo will be present in the construct. Any sequence present in the synthetic oligo will also be present in the construct. The capture oligo and the synthetic oligo may either or both have a PCR handle (i.e., a primer binding site, a "universal primer binding site", a capture tag, a sequencing adaptor, or similar). Thus, in preferred embodiments, the attachment 115 creates a construct that includes a first PCR handle, an optional functional sequence such as a sample barcode and/or a cell barcode, a hybrid capture portion of the capture oligo (e.g., a poly-T region), a portion of the cDNA, the location of the random cut site, and a second PCR handle.

Because the construct is preferably a contiguous DNA molecule with PCR handles at both ends, it is amenable to amplification 123 by, for example, polymerase chain reaction (PCR). The optional functional sequence may be a cell barcode. More specifically, the capture oligo may be one of a plurality of capture oligos that are attached to a solid support such as a bead, e.g., a hydrogel bead. All capture oligos may share one common barcode (reasonably referred to as a "bead barcode"). If the bead is isolated in an aqueous partition with a single cell and the capture oligos are used to anneal to, and capture, RNA molecules from the single cell, then the common barcode of the bead becomes a cell barcode. This is because, downstream, after sequencing 127, the presence of the cell barcode sequence in a sequence read is useful to map that sequence read back to the single cell associated with that bead. Thus, a barcode in the construct may be used as a cell barcode. All such constructs from a single cell may be amplified 123.

The constructs may include sequence platform specific primers (e.g., P5 and P7) or those may be added by a round of amplification, e.g., PCR. Amplification 123 produces amplicons which may be sequenced 127.

In particular, methods of the invention are useful to create sequence libraries. Those libraries may be sequenced 127 to identify transcript abundances, or gene expression levels, of single cells. In generally, it is understood that the product of amplification step 123 produces a sequencing library. However, depending on the sequencing technology being used (e.g., single-molecule long-read sequencing versus short-read ensemble sequencing), the distribution of steps, and the desired storage times or conditions for certain library prep products, the product of attachment 115 could be considered a sequencing library. Also, a library produced by amplification 123 may freely be subject to further rounds of amplification (e.g., entirely at the preference of a user), e.g., after being shipped to a different location. For example, RNA capture, cDNA synthesis, and a first round of amplification may be performed at a research or clinical services laboratory to create a sequencing library, which may be stored in a tube such as a microcentrifuge tube. The sequencing library may be shipped (e.g., on dry ice) to a genomics core facility for sequencing. The genomics core facility may provide sequence data via a server or data room. The research or clinical services laboratory or another party may access the sequence data to initiate mapping and/or deduplication, which may occur in an online server, in the cloud, or on a local computer. In general, a sequencing library includes DNA copies of target nucleic acids from a sample of interest with PCR handles or adaptors attached at ends. The amplicons may be stored, for example, at −20 degrees Celsius, or may be analyzed. Analyzing amplicons preferably involves sequencing. The sequencing library may be sequenced 127.

Sequencing 127 may be performed by any method known in the art. An example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequencing. After nucleotide incorporation, a laser is used to excite the fluorophores, and an image is captured, and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference. In preferred embodiments, an Illumina Mi-Seq sequencer is used.

Sequencing 127 creates sequence reads, i.e., a record of a sequence of bases from at least a part of a nucleic acid. The sequence reads may be analyzed to determine expression of RNA associated with genes based on unique reads that correspond to those genes. Analyzing the sequence reads may be performed using known software and following multistep procedures that are known in the art. For example, first, the quality of each sequence read, i.e., FASTQ sequence, may be assessed using the software FASTQC. Next, the reads may be trimmed using, for example, using Trimmomatic software. See Bolger, 2014, Trimmomatic: a flexible trimmer for Illumina sequence data, Bioinformatics 30(15):2114-2120, incorporated by reference. The trimmed sequence reads may then be mapped to a human genome using with, for example, HISAT2 software. HISAT2 output files in a SAM (sequence alignment/map format), which may be compressed to binary sequence alignment/map files. Other methods useful for processing and analyzing sequence reads are discussed in U.S. Pat. No. 8,209,130, which is incorporated by reference. Determining gene expression generally involves counting numbers of unique sequence reads that uniquely map to a human reference genome. Mapping reads to a reference to identify genes may be performed using computer software packages known in the art.

An important benefit of the invention is that mapping reads to a reference and identifying genes gives a quantitative result when reads are deduplicated to yield one read per mRNA from which those reads originated. Because each mRNA is typically copied into cDNA and each cDNA is typically copied into an unpredictably large number of amplicons in the sequencing library, and because each library member is often amplified or read redundantly as part of a sequencing technique, a number of raw sequence reads does not necessarily correlate to numbers of input molecules from the single cells. Nevertheless, one cell may include abundant transcripts that map to one gene. Here, compositions and methods of the invention give each cDNA a unique intrinsic identifier that can be identified within, and used to deduplicate, sequence reads. After those sequence reads are identified by gene and deduplicated, then counts of those reads provide a quantitative measure of gene expression levels.

As discussed, methods of the invention are useful for scRNA-Seq and specifically for expression analysis. In preferred embodiments, cells are isolated into, and lysed within, aqueous partitions with capture oligos. The capture oligos anneal to RNAs released from the cells. The capture oligos preferably include partition-specific barcodes and PCR handles. Once the capture oligos have hybridized to the RNAs, those duplexes may be released from partitions and pooled at any subsequent stage. Because capture oligos with partition-specific barcodes are used to capture and tau RNA from cells isolated in the partition, any arbitrary number of cells may be captured in parallel (simultaneously). Because the RNAs are tagged with a cell barcode during hybrid capture (e.g., aka a partition-specific barcode or a bead barcode), if those duplexes are pooled and ultimately sequenced, the cell barcodes in the sequencing data can be used to "bin" the sequence data by original cell, i.e., assign each sequence read (or assembled contigs or sequences therefrom) back to originating cells.

Multiplexing preferably involves isolating cells and the capture oligos into partitions. Any suitable partitions may be used. The partitions may be any suitable partition in a pico-, nano-, or microtiter plate or substrate, or fluidic harbors (see, e.g., US Pub 2010/0041046 A1, incorporated by reference), chambers (see, e.g., 20210178395 A1, incorporated by reference), regions defined within a fluidic device (see, e.g., 20200269248 A1, incorporated by reference), others, or combinations thereof. In certain embodiments, the partitions are aqueous partitions in an immiscible liquid, e.g., slugs or droplets surrounded or separated by oil within a microfluidic device. A microfluidic device may use channels to mix samples and reagents and form droplets in an immiscible carrier fluid. In certain embodiments, the partitions are a plurality of droplets that are formed essentially simultaneously. Methods may be performed with a sample comprising a mixture with cells, and preferably template particles. The mixture preferably includes two immiscible fluids such as an aqueous fluid and oil. The mixture is sheared, e.g., vortexed, to generate an emulsion with template particles that serve to template the formation of droplets and segregate individual cells into the droplets. Because the cells are individually segregated into droplets, the cells may be individually profiled in parallel. This method provides a massively parallel, analytical workflow for analyzing single cells that is inexpensive, scalable, and accurate.

For example, methods of the invention may include combining template particles with cells in a first fluid and then adding a second fluid that is immiscible with the first fluid to the mixture. The first fluid is preferably an aqueous fluid. While any suitable order may be used, in some instances, a tube may be provided comprising the template particles. The tube can be any type of tube, such as a sample preparation tube sold under the trade name Eppendorf, or a blood collection tube, sold under the trade name Vacutainer. The sample may be a blood sample and may be added directly to the tube using a pipette.

The fluids can be sheared to generate a monodisperse emulsion with droplets. To generate a monodisperse emulsion, methods includes a step of shearing the mixture provided by combining cells and template particles in an aqueous fluid with the immiscible fluid. Any suitable method or technique may be utilized to apply a sufficient shear force to the mixture. For example, the mixture may be sheared by flowing the second mixture through a pipette tip. Other methods include, but are not limited to, shaking the mixture with a homogenizer (e.g., vortexer), or shaking the mixture with a bead beater. In some embodiments, vortex may be performed for example for 30 seconds, or in the range of 30 seconds to 5 minutes. The application of a sufficient shear force breaks the mixture into monodisperse droplets that encapsulate one of a plurality of template particles.

After vortexing, a plurality (e.g., thousands, tens of thousands, hundreds of thousands, one million, two million, ten million, or more) of aqueous partitions is formed essentially simultaneously. Vortexing causes the fluids to partition into a plurality of monodisperse droplets. A substantial portion of droplets will contain a single template particle and a single target cell. Droplets containing more than one or none of a template particle or target cell can be removed, destroyed, or otherwise ignored.

The next step of the method is to lyse the cells. Cell lysis may be induced by a stimulus, such as, for example, lytic reagents, detergents, or enzymes. Reagents to induce cell lysis may be provided by the template particles via internal compartments. Preferably, lysing involves heating the monodisperse droplets to a temperature sufficient to release lytic reagents contained inside the template particles into the monodisperse droplets. This accomplishes cell lysis of the target cells, thereby releasing nucleic acids, such as RNA, and preferably mRNA, inside of the droplets that contained the target cells.

After lysing target cells inside the droplets, mRNA is released. The mRNA may be used to create a sequencing library. Methods and systems of the invention may use template particles to template the formation of monodisperse droplets and isolate single target cells. The disclosed template particles and methods for targeted library preparation thereof leverage the particle-templated emulsification technology described in Hatori, 2018, Particle-templated emulsification for microfluidics-free digital biology, Anal Chem 90(16):9813-9820, incorporated by reference. Essentially, micron-scale beads (such as hydrogels) or "template particles" are used to define an isolated fluid volume surrounded by an immiscible partitioning fluid and stabilized by temperature insensitive surfactants.

In practicing the methods as described herein, the composition and nature of the template particles may vary. For instance, in certain aspects, the template particles may be microgel particles that are micron-scale spheres of gel matrix. In some embodiments, the microgels are composed of a hydrophilic polymer that is soluble in water, including alginate or agarose. In other embodiments, the microgels are composed of a lipophilic microgel.

Figure 2:
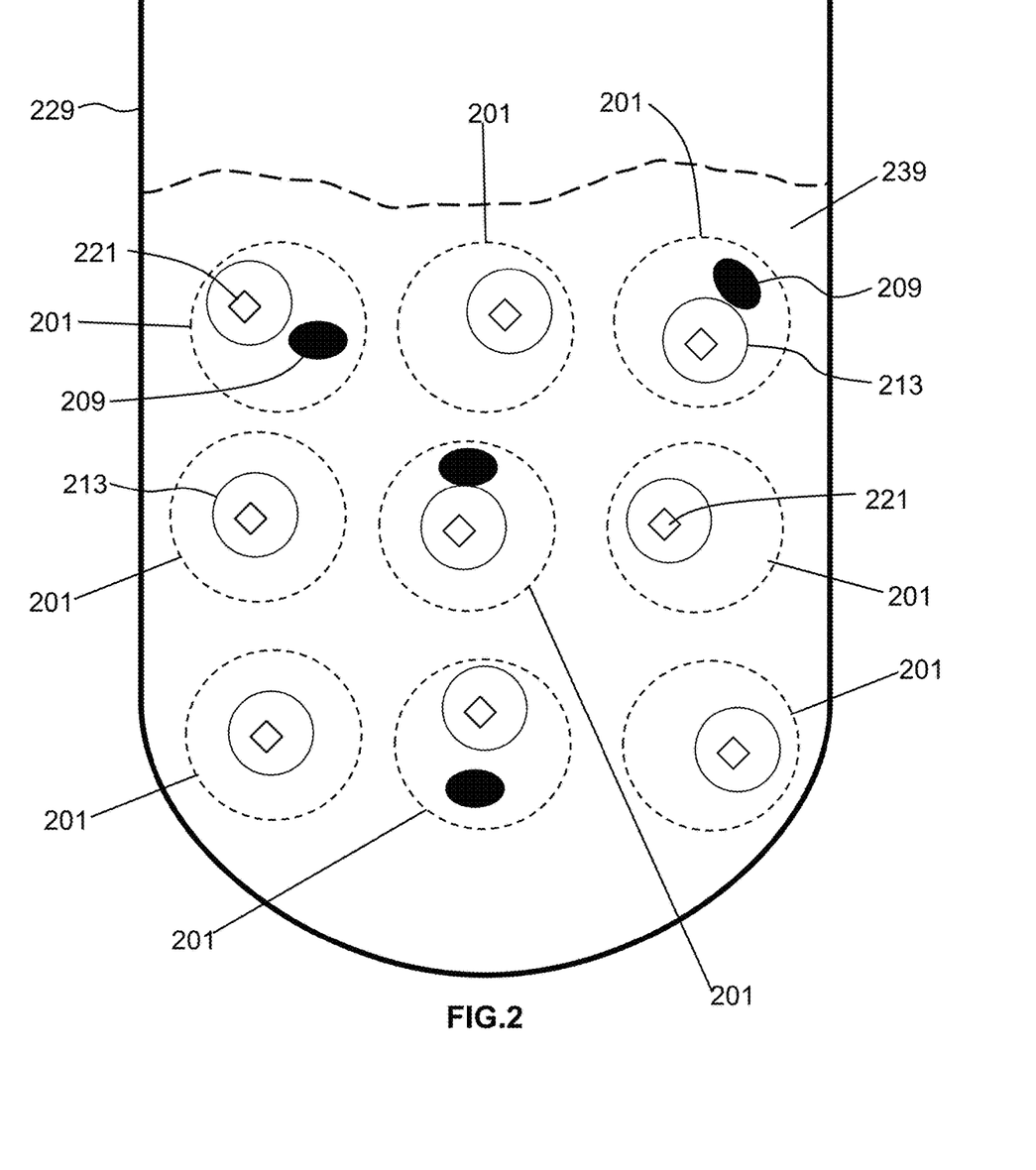
FIG. 2 illustrates cell encapsulation in droplets for scRNA-seq.

FIG. 2 illustrates a sample prep tube 229 comprising droplets 201. In particular, the sample prep tube 229 comprises a plurality of monodisperse droplets generated by shearing a mixture 239 according to preferred methods of the invention. Preferably, each of the droplets 201 includes, on average, one template particle 213 and zero or one single target cell 209. The template particles 213 may comprise crater-like depressions (not shown) to facilitate capture of single cells 209. The template particles 213 may further comprise an internal compartment 221 to deliver one or more reagents into the droplets 201 upon stimulus.

In some embodiments, the template particles contain internal compartments. The internal compartments of the template particles may be used to encapsulate reagents that can be triggered to release a desired compound, e.g., a substrate for an enzymatic reaction, or induce a certain result, e.g. lysis of an associated target cell. Reagents encapsulated in the template particles' compartment may be without limitation reagents selected from buffers, salts, lytic enzymes (e.g. proteinase k), other lytic reagents (e. g. Triton X-100 Tween-20, IGEPAL), nucleic acid synthesis reagents, or combinations thereof.

Lysis of single target cells occurs within the monodisperse droplets and may be induced by a stimulus such as heat, osmotic pressure, lytic reagents (e.g., DTT, beta-mercaptoethanol), detergents (e.g., SDS, Triton X-100, Tween-20), enzymes (e.g., proteinase K), or combinations thereof. In some embodiments, one or more of the said reagents (e.g., lytic reagents, detergents, enzymes) is compartmentalized within the template particle. In other embodiments, one or more of the said reagents is present in the mixture. In some other embodiments, one or more of the said reagents is added to the solution comprising the monodisperse droplets, as desired.

In preferred embodiments, template particles 213 comprise a plurality of capture probes. Generally, the capture probe of the present disclosure is an oligonucleotide. In some embodiments, the capture probes are attached to the template particle's material, e.g. hydrogel material, via covalent acrylic linkages. In some embodiments, the capture probes are acrydite-modified on their 5' end (linker region). Generally, acrydite-modified oligonucleotides can be incorporated, stoichiometrically, into hydrogels such as polyacrylamide, using standard free radical polymerization chemistry, where the double bond in the acrydite group reacts with other activated double bond containing compounds such as acrylamide. Specifically, copolymerization of the acrydite-modified capture probes with acrylamide including a cross-linker, e.g. NX-methylenebis, will result in a crosslinked gel material comprising covalently attached capture probes. In some other embodiments, the capture probes comprise acrylate terminated hydrocarbon linker and combining the said capture probes with a template particle will cause their attachment to the template particle.

In some embodiments, after cell suspensions are introduced to template particles in a pre-equilibrated buffer, droplets are generated by vortexing the mixture to capture single cells with individual template particles. The resulting emulsion may be heated on a thermocycler to induce cell lysis. Cell lysis releases the contents of the cell and exposes those contents, including mRNA, to the particle 213. The invention provides steps for RNA capture and library preparation using those particles and released mRNA.

Figure 3:
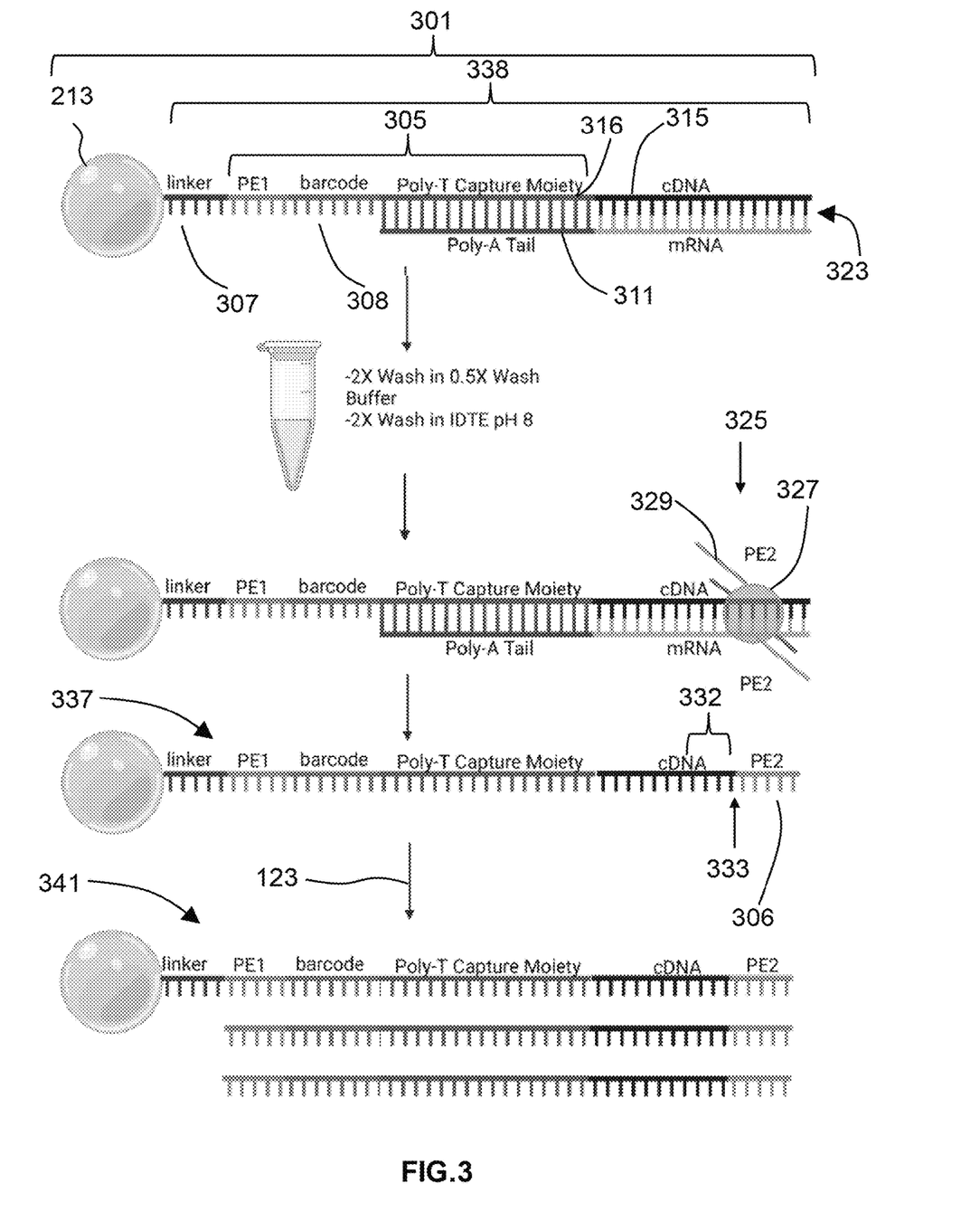
FIG. 3 diagrams RNA capture and library preparation by methods of the invention.

FIG. 3 diagrams RNA capture and library preparation according to methods of the invention. As shown, particle 213 is linked to a capture oligo 305. The capture oligo 305 anneals to an mRNA 311. In some embodiments, poly-T tails of the capture oligos anneal to and capture RNA released by lysis. Particle-bound capture oligos in this application may comprise an acrydite linker, a PEI priming sequence, a particle barcode, optionally a random sequence, and a poly-T capture moiety. A polymerase (not pictured) extends the capture oligo 305 to form a cDNA 315. The cDNA 315 and capture oligo 305 in combination with the mRNA 311 form a duplex 323. This duplex is stably linked to the bead 213. At this stage, it is suitable to break the droplets and pool their contents, wash in buffer, and proceed in library preparation.

A transposase complex 325 (sometimes called a transposasome) is introduced. The transposase complex 325 includes a dimer that includes two of a transposase 327 and two transposon end sequences 329. Here, the transposon end sequences 329 are depicted as both being paired-end 2 end (PE2) sequences, which will cooperate with paired-end 1 (PE1) sequences in the capture oligo 305 in subsequent amplification and sequence steps. In the depicted method, the transposase randomly cuts the cDNA/mRNA duplex 323 thereby defining a random cut site 333. In a downstream step, read 2 of paired-end sequencing will include the first segment of bases in the cDNA 315 adjacent the random cut site 333.

Attachment 115 of the end sequence 329 to the cDNA 315 at the random cut site 333 produces a construct 337. The construct 337 is a contiguous DNA molecule that includes a first PCR handle (PE1), a cell barcode, a capture segment, a portion of the cDNA 315 terminating at the random cut site 333, and a second PCR handle (PE2).

Amplification 123 of the construct 337 yields amplicons 341. In some embodiments, constructs are amplified with a P5-PE1 hybrid oligo and P7 index primer directly into a sequencing library. The library may be sequenced to assess RNA expression, for example, as described in Hrdlickova, 2017, RNA-Seq methods for transcriptome analysis, Wiley Interdisc Rev RNA 8(1):10.1002, incorporated by reference.

Constructs or amplicons may include certain primer and index sequences or copies thereof, such as, P5s and P7s. Those sequences may be any arbitrary sequence useful in downstream analysis. For example, they may be additional universal primer binding sites or sequencing adaptors. For example, either or both of the P5s and P7s may be arbitrary universal priming sequence (universal meaning that the sequence information is not specific to the naturally occurring genomic sequence being studied, but is instead suited to being amplified using a pair of cognate universal primers, by design). The index segment may be any suitable barcode or index such as may be useful in downstream information processing. It is contemplated that the P5 sequences, the P7 sequence, and the index segment may be the sequences use in NGS indexed sequences such as performed on an NGS instrument sold under the trademark ILLUMINA, and as described in Bowman, 2013, Multiplexed Illumina sequencing libraries from picogram quantities of DNA, BMC Genomics 14:466 (esp. in FIG. 2), incorporated by reference.

Importantly, a transposase 327 is used to randomly cut the cDNA 315. This may be performed using a transposase such as Tn5. See Lin, 2020, RNA sequencing by direct tagmentation of RNA/DNA hybrids, PNAS117 (6) 2886-2893, incorporated by reference. In brief, the Tn5 transposase randomly binds and cuts double-stranded RNA/DNA and attaches its end sequence to the random cut site.

Accordingly, some embodiments of the invention use Tn5 transposase to directly tagment RNA/DNA hybrids and form polynucleotide libraries with intrinsic molecular identifiers (essentially unique sequences of bases originating in genetic material of the organism or biological system being studied). In particular, Tn5, a RNase H superfamily member, binds to RNA/DNA hybrids similarly as to dsDNA and effectively cuts randomly and then ligates a desired oligo onto the hybrid. The desired oligo is preferably a PCR handle (aka a universal primer binding site, a sequencing adaptor, a synthetic oligo of known sequence to which a PCR primer anneals, etc.). Methods of the invention may be used with various amounts of input sample, from single cells to large numbers of cells, with a dynamic range spanning numerous orders of magnitude.

Figure 4:
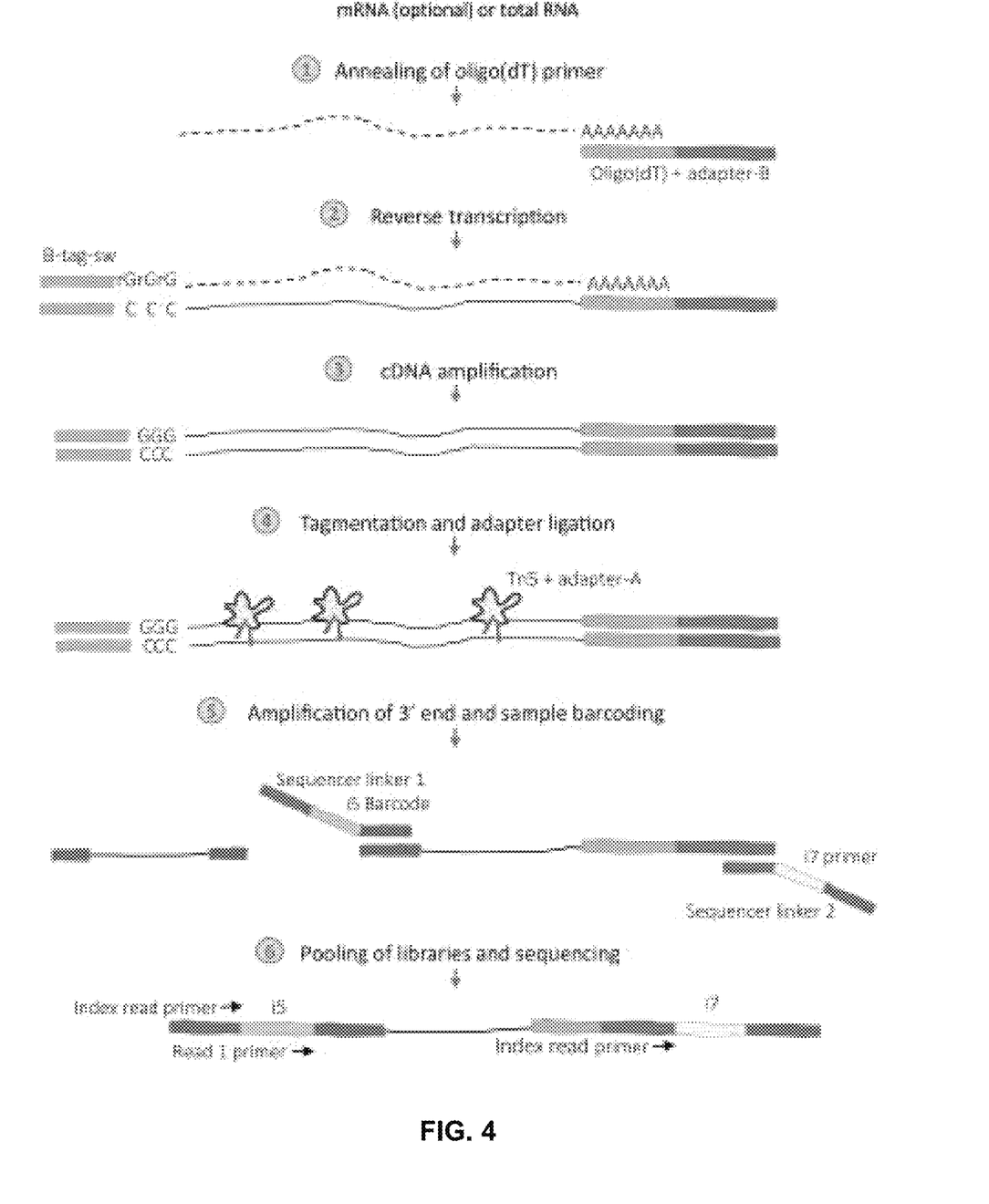
FIG. 4 shows IMI libraries made in workflows using template switching oligos (TSOs).

FIG. 4 shows a workflow for directional tagmentation that works with template switching oligos (TSOs). The illustrated technique may be employed in hybrid workflows where one is using TSOs for some other benefit and one also want to use IMIs. This tagmentation approach is useful for 3' end capture and analysis of mRNAs. The steps of the method are shown. In brief, mRNA or total RNA from lysed cells are mixed with an oligo and incubated at 65° for 3 min. The oligo may include specific primers for amplifying final libraries, such as an adapter-B sequence complementary to an i7 primer. The oligo may further include a poly-T sequence of, for example, 30 nucleotides that hybridizes with poly-A tails of mRNA. Importantly, the use of this oligo to prime a first strand cDNA synthesis may result in libraries enriched for the 3' end of mRNA.

Reverse transcription can be performed using a reverse transcriptase such as the reverse transcriptase sold under the trade name SMARTSCRIBE by Takara Bio optionally in the presence of a template switching oligo (TSO). The template switching oligo allows for template switching at the 5' end of the mRNA molecule to incorporate an oligo such as a universal 3' sequence during first strand cDNA synthesis. Synthesis of the first cDNA strand may be performed using a thermocycler at 42 degrees Celsius for 1 h, followed by 15 minutes at 70 degrees Celsius to inactivate the reverse transcriptase. Afterwards, the cDNA may be amplified. The cDNA may be amplified by PCR using commercially available kits such as the kit sold under the trade name OneTaq HS by New England Biolabs. After amplification, the RNA/DNA duplexes may be subjected to tagmentation and adapter ligation.

During tagmentation and adapter ligation, Tn5 bound adapter (adapter-A) complexes bind with the double RNA/DNA duplexes. The duplexes are cut by the enzymatic activity of the Tn5 complexes and the adapters ("Adaptor A") are ligated. Importantly, Tn5 cuts at a random site. Afterwards, the products of the tagmentation reaction may be amplified using the adapters. As shown, an i7 primer anneals to Adapter B and an i5 primer anneals to Adapter A. In this depicted embodiment (as drawn) the read 1 primer will read into a segment of an amplicon adjacent the random cut site. Because the cut site is random, a sequence of bases in that segment is essentially unique. Because the segment is in the amplicon copy of the cDNA, itself a copy of the mRNA, the sequence of the basis is intrinsic to the mRNA, i.e., is a sequence from genetic material of the organism being studied. Because the sequence of bases is essentially unique, a read 1 sequence read will include a unique, intrinsic molecular identifier. More specifically, all sequence reads from the read 1 primer from this library member will include the identical copies of that unique, intrinsic molecular identifier (IMI). Thus the figure illustrates that IMIs are compatible with workflows that include or use TSOs.

After sequencing, reads with identical gene-mapping and identical IMIs can be "collapsed", and a count of only unduplicated such reads is a quantitative measure of gene transcripts in the sample, i.e., the single cell.

As shown in FIG. 4, the use of IMIs is compatible with RNA capture without necessarily requiring any bead-linked capture oligos. That is, capture oligos may be free in solution (as opposed to linked to a solid support). Methods of the invention are also compatible with the use of capture oligos that are linked to a solid support such as a bead.

Figure 5:
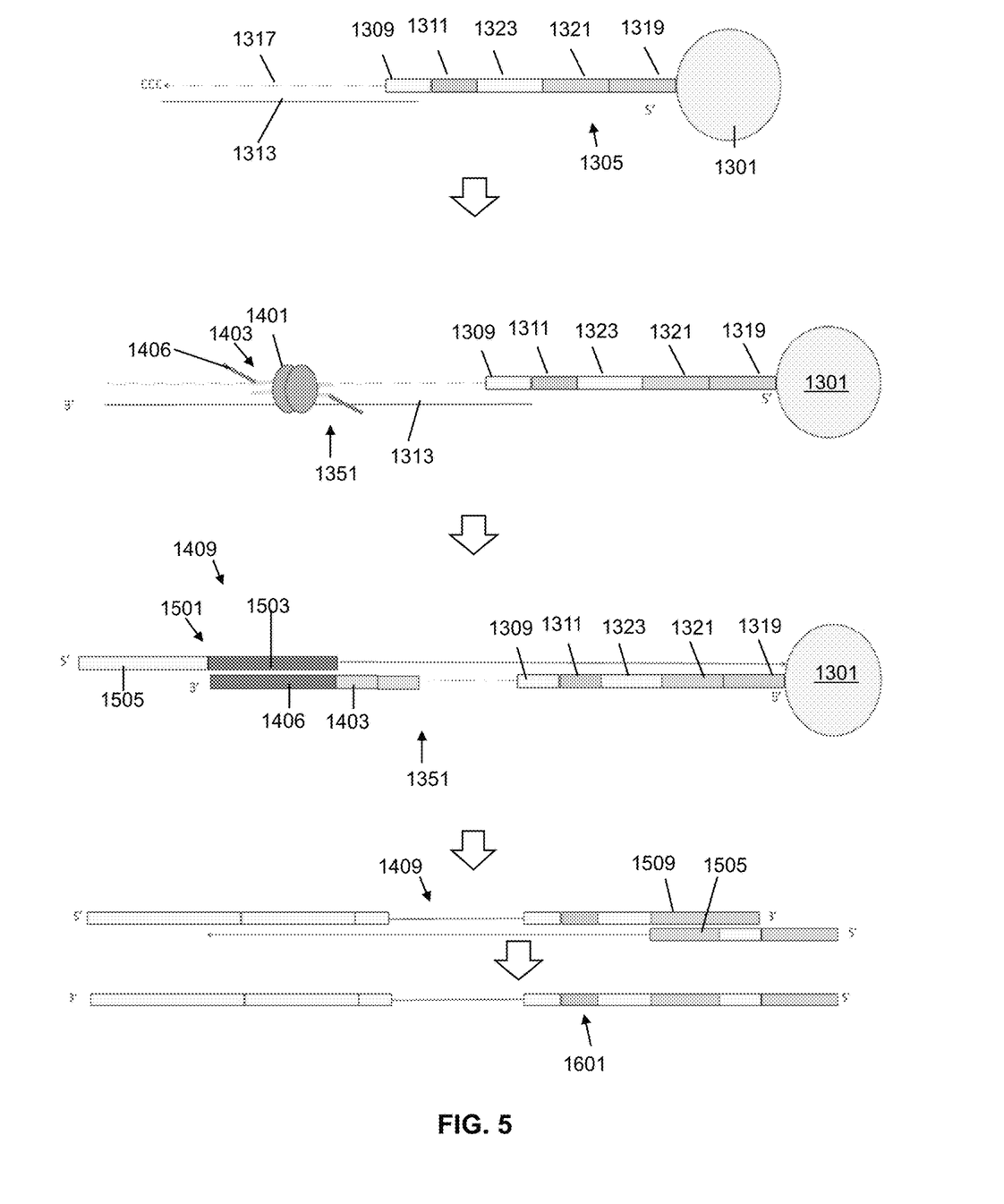
FIG. 5 shows IMI libraries with beads and next-generation sequencing (NGS) adaptors.

FIG. 5 shows a method for making libraries that include IMIs using capture oligos linked to a solid support. This embodiments shows the creating of a sequencing library that includes certain next-generation sequencing (NGS) adaptors. The solid support may be bead and library preparation may be performed using a microfluidic device (e.g., to encapsulate beads, cells, and reagents into droplets). In some embodiments, beads decorated with capture oligos are used to simultaneously form a monodisperse emulsion that includes a plurality of droplets. Each droplet includes, on average, one bead and one or zero cells. Because the beads are particles that serve as templates cause the droplets (or aqueous partitions) to form (e.g., when a mixture is vortexed), the droplets may be referred to as particle-templated instant partitions (PIPs), the beads maybe referred to template particles, and sequencing from such libraries may be referred to as PIP-seq. In the illustrated embodiment, a template particle 1301 is linked to a capture oligo 1305. As shown, the particle 1301 is linked to (among other things) mRNA capture oligos 1305 that include a 3' poly-T region 1309 (although sequence-specific primers or random N-mers may be used). Where the sample includes cell-free RNA, the capture oligo hybridizes by Watson-Crick basepairing to a target in the RNA and serves as a primer for reverse transcriptase, which makes a cDNA copy of the RNA. Where the initial sample includes intact cells, the same logic applies but the hybridizing and reverse transcription occurs once a cell releases RNA (e.g., by being lysed).

In preferred embodiments, the target RNAs are mRNAs 1313. Where the target RNAs are mRNAs, the particles 1301 may include mRNA capture oligos 1305 used to at least synthesize cDNA 1317 as a copy of an mRNA 1313. The particles 1301 may further include cDNA capture oligos with 3' portions that hybridize to cDNA copies of the mRNA. For the cDNA capture oligos, the 3' portions may include gene-specific sequences or hexamers. As shown, each of the mRNA capture oligos 1305 may include, from 5' to 3', a SMART site 1319, a PEI sequence 1321, a cell or droplet barcode 1323, and a poly-T segment 1309. Optionally, the capture oligos may include a UMI 1311.

As shown, the capture oligo 1305 hybridizes to the mRNA 1313. A reverse transcriptase binds and initiates synthesis of a cDNA copy 1317 of the mRNA 1313 to make an RNA/DNA hybrid. Note that the mRNA 1313 is connected to the particle 1301 non-covalently, by complementary base-pairing. The cDNA 1317 that is synthesized may be covalently linked to the particle 1317 by virtue of the phosphodiester bonds formed by the reverse transcriptase.

A transposase 1401 binds to the RNA/DNA hybrid. The transposase 1401, which is preferably a Tn5 transposase, is attached with adapters 1406 for attaching onto the 5' end of the cDNA 1317. The Tn5 cuts the RNA/DNA hybrid at a random cut site and the adapters 1406 are ligated onto the random cut site of the cDNA 1317. Preferably the adapter 1406 includes a primer handle 1403 for copying/amplification. At this stage, RNaseH may be introduced to degrade the mRNA 1313.

In some embodiments, sequencing adapter 1501 is extended to create a dsDNA 1409. The adapter 1501 includes a first sequence 1503 complementary to the primer handle 1403 and a sequencing primer 1505, such as P7. The adapter 1501 will hybridize to, and prime the copying of, cDNA to create a dsDNA 1409 with the sequencing adapter. Afterwards, the polynucleotide can be separated from the particle and made into a final library product. What is important is that the cDNA 1317 and thus also the dsDNA 1409 has a segment adjacent the random cut site 1351 with sequence intrinsic to the mRNA 1313. When that segment is sequenced from primer handle 1403, the resultant sequence reads include the intrinsic sequence.

Amplification produces a final library product 1601. In this example, the final library product 1601 is formed by the PCR-based extension a P5-PE1 primer 1505 that is complementary to the PEI 1509 of the released polynucleotide 1409. Extension of the P5-PE1 primer 1505 by PCR creates the final library product 1601. In some embodiments, the P5-PE1 primer 1505 may include indexes, such as an IS index, and a P5 index. The final library product may be amplified by PCR in advance of sequencing.

Any one of the above described strategies and methods, or combinations thereof may be used in the conjunction particle-templated emulsions. For example, methods may be used for single cell expression profiling, which may include combining target cells with a plurality of template particles in a first fluid to provide a mixture in a reaction tube. The mixture may be incubated to allow association of the plurality of the template particles with target cells. A portion of the plurality of template particles may become associated with the target cells. The mixture is then combined with a second fluid which is immiscible with the first fluid. The fluid and the mixture are then sheared so that a plurality of monodisperse droplets is generated within the reaction tube. The monodisperse droplets generated comprise (i) at least a portion of the mixture, (ii) a single template particle, and (iii) a single target particle. Of note, in practicing methods of the invention provided by this disclosure a substantial number of the monodisperse droplets generated will comprise a single template particle and a single target particle, however, in some instances, a portion of the monodisperse droplets may comprise none or more than one template particle or target cell.

In some aspects, generating the template particles-based monodisperse droplets involves shearing two liquid phases. The mixture is the aqueous phase and, in some embodiments, comprises reagents selected from, for example, buffers, salts, lytic enzymes (e.g. proteinase k) and/or other lytic reagents (e. g. Triton X-100, Tween-20, IGEPAL, bm 135, or combinations thereof), nucleic acid synthesis reagents e.g. nucleic acid amplification reagents or reverse transcription mix, or combinations thereof. The fluid is the continuous phase and may be an immiscible oil such as fluorocarbon oil, a silicone oil, or a hydrocarbon oil, or a combination thereof. In some embodiments, the fluid may comprise reagents such as surfactants (e.g. octylphenol ethoxylate and/or octylphenoxypolyethoxyethanol), reducing agents (e.g. DTT, beta mercaptoethanol, or combinations thereof).

Some methods of the disclosure use oligos. Oligos, sometimes referred to as oligonucleotides, are sequences of contiguous nucleotides of DNA, RNA, or a mixture thereof. Preferably, oligos comprise DNA. However, in certain embodiments, oligos may comprise RNA. In other embodiments, oligos may comprise a mixture of DNA and RNA. Oligos may comprise noncanonical nucleotides, such as, synthetic nucleotides that have been modified to incorporate certain biomolecular properties. The length of the oligo is usually denoted by "-mer". For example, an oligo of six nucleotides is a hexamer, or 6-mer, while one of 25 nucleotides may be referred to as a 25-mer. An oligo may include other features such one or more conformationally-restricted nucleic acid or a locked nucleic acid (LNA) bases or phosphorothioate inter-base linkages, to improve binding stability or residence times.

FIG. 3 shows a composition 301 comprising; a solid support (e.g. particle 213) having attached thereto a plurality of DNA molecules (e.g. nucleic acid construct 337), each DNA molecule (e.g. nucleic acid construct 337) of the plurality comprising a capture sequence 316 (e.g. capture region) complementary to a portion of an RNA 311, a segment of cDNA 315 containing a unique identifier sequence 332 that is intrinsic to the RNA 311 and unique with respect to other members of the plurality of DNA molecules (e.g. nucleic acid construct 337), a linker 307, a cell identification barcode 308, and a primer binding sequence 306.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A composition comprising;
a solid support having attached thereto a plurality of DNA molecules, each DNA molecule of the plurality comprising
a capture sequence complementary to a portion of an RNA,
a segment of cDNA containing an identifier sequence that is intrinsic to the RNA and unique with respect to other members of the plurality of DNA molecules, and
a primer binding sequence.

2. The composition of claim 1, wherein the identifier sequence that is intrinsic to the segment of cDNA is from about 5 to about 20 base pairs in length.

3. The composition of claim 1, wherein the DNA molecule comprises a coding region.

4. The composition of claim 1, further comprising a linker for attachment to the solid support.

5. The composition of claim 4, wherein the attachment is a covalent attachment.

6. The composition of claim 1, wherein the primer binding sequence is ligated to the DNA using transposase.

7. The composition of claim 6, wherein the transposase cleaves the DNA to generate the identifier sequence and insert a paired-end sequence.

8. The composition of claim 1, wherein the portion of RNA is a poly-T region and the capture sequence comprises a poly-A region.

9. A composition comprising;
a particle having attached thereto a plurality of nucleic acid constructs, wherein each construct is a contiguous DNA molecule that includes:
a capture oligo complementary to a portion of an RNA,
a segment of cDNA containing an identifier sequence that is intrinsic to the RNA and unique, and
a primer binding sequence.

10. A composition comprising:
a solid support; and
a nucleic acid construct attached to the solid support, the nucleic acid construct comprising a linker for attachment to the solid support, a cell-identification barcode, a capture region, and a region of cDNA comprising a unique identifier sequence that is intrinsic to the RNA.

11. The composition of claim 10, further comprising a transposase that functions to cleave the cDNA, thereby generating the unique identifier sequence, and a paired-end sequence for hybridization to a sequencing surface.

12. The composition of claim 11, wherein the transpose cleaves the cDNA at a cut site that is random or cannot be predicted and attaches the paired-end sequence to the cDNA at the cut site.

13. The composition of claim 12, wherein the unique identifier sequence is defined by a plurality of nucleic acid bases in a segment of the cDNA adjacent to the cut site.

14. The composition of claim 12, further comprising a plurality of paired-end sequence-ligated cDNAs, each comprising an identifier sequence in the cDNA adjacent a random cut site.

15. The composition of claim 14, wherein sequence reads from the plurality of cDNAs can be deduplicated to quantify RNAs captured on the solid support.

16. The composition of claim 10, wherein the region of cDNA has been randomly cleaved at a random cut site, and wherein a synthetic oligo has been attached at the random cut site.

17. The composition of claim 16, wherein the cDNA has been randomly cleaved by a restriction enzyme or sonication, and wherein the synthetic oligo has been attached by a ligase.

18. The composition of claim 16, wherein the cDNA has been cleaved by an nuclease and the synthetic oligo has been attached by a ligase.

19. The composition of claim 16, wherein the unique identifier sequence is defined by a plurality of nucleic acid bases in a segment of the cDNA adjacent to the cut site.

20. The composition of claim 19, wherein the plurality of nucleic acid bases are copied from genetic material of an organism.

21. The composition of claim 10, further comprising a plurality of the solid supports, each solid support attached to cDNA copies of RNAs from a single cell, wherein each cDNA copy has a unique identifier defined by nucleic acid bases in a segment of that cDNA copy adjacent to a random cut site, wherein the RNAs from a single cell can be quantified by sequencing the RNAs and deduplicating sequence reads by the unique identifier.

22. The composition of claim 10, wherein the solid support comprises a hydrogel bead linked to a plurality of capture oligos.

23. The composition of claim 22, further comprising a plurality of the hydrogel beads, each isolated in an aqueous partition.

* * * * *